United States Patent [19]

Zirm

[11] Patent Number: 4,955,887
[45] Date of Patent: Sep. 11, 1990

[54] OPTICAL SURGICAL INSTRUMENT

[75] Inventor: Mathias Zirm, Innsbruck, Austria

[73] Assignee: Storz Instrument Company, St. Louis, Mo.

[21] Appl. No.: 350,464

[22] Filed: May 11, 1989

[30] Foreign Application Priority Data

May 11, 1988 [DE] Fed. Rep. of Germany ....... 3816059

[51] Int. Cl.$^5$ .............................................. A61B 17/32
[52] U.S. Cl. .................... 606/107; 606/162; 606/170
[58] Field of Search ............... 606/107, 170, 171, 138, 606/167, 162

[56] References Cited

U.S. PATENT DOCUMENTS

| 4,384,406 | 5/1983 | Tischlinger | 606/138 |
|---|---|---|---|
| 4,538,611 | 9/1985 | Kelman | 606/107 |
| 4,577,629 | 3/1986 | Martinez | 606/171 |
| 4,699,140 | 10/1987 | Holmes et al. | 606/107 |
| 4,706,666 | 11/1987 | Sheets | 606/107 |
| 4,759,359 | 7/1988 | Willis et al. | 606/107 |

Primary Examiner—Robert A. Hafer
Assistant Examiner—Kerry Owens
Attorney, Agent, or Firm—Brooks & Kushman

[57] ABSTRACT

This ophthalmological instrument is intended to aid in the removal of the mount (lens haptic) of an artificial intraocular lens from the eye, allowing the portion of the mount located behind the iris to be captured and severed by means of an axially sliding cutter installed inside the instrument head, in a tubular guide. In order to capture, sever and remove the mount from the eye in one single operation, it is the intent for the tubular guide to have a lateral opening at its tip, which is closed off by a stop plate at its face end. Parallel with the cutter, a holder with axially sliding motion is supported inside the tubular guide, which may be moved to contact the stop plate, independent of the cutter. The loop end to be severed is inserted sideways into the opening and, initially, clamped down by the holder against the stop plate, only to be severed by the cutter. Subsequently, the severed loop end is removed from the eye while still clamped down by the holder.

19 Claims, 2 Drawing Sheets

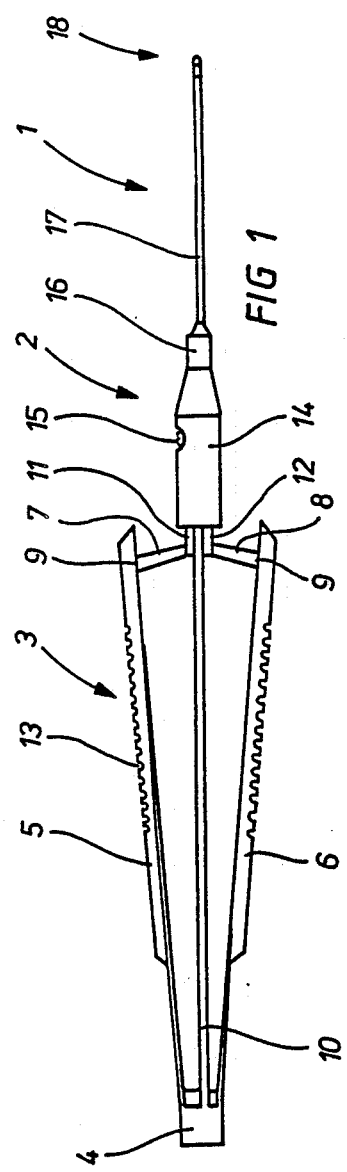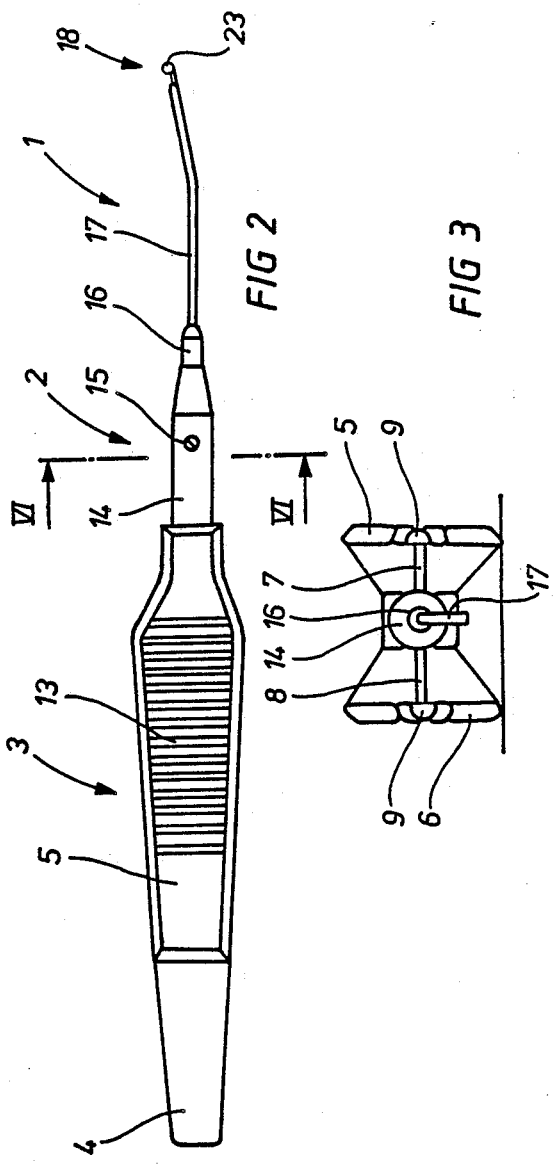

OPTICAL SURGICAL INSTRUMENT

BACKGROUND OF THE INVENTION

This invention refers to an ophthalmological instrument for the removal of an artificial ocular lens mount from the eye.

Such an instrument has been known to exist in a variety of configurations.

For example: the company Katena Products, Inc. is marketing such an ophthalmological instrument under the name "LensLoop Amputator". This instrument, however, is only designed to cut off the haptic, without being able to remove it from the eye.

The removal of an artificial lens (so-called intraocular lens) from the eye is frequently necessary. In the 50's it was the so-called "Tannheim Lenses" which, after implantation, had to be removed again in approximately 50% of all cases. New lenses designed in the years following had fewer side effects, but their removal is increasingly necessary. This is caused by a growing number of implantations (approximately one (1) million annually) and a multitude of lens designs (approximately 500) which, in part, do not live up to their expectations. Also, for many patients (especially in the U.S.A.), an erroneous preoperative diagnosis of the power level required for the optical lens unit is the reason to seek a change of lenses. Today, most lens implantations are performed in areas of the eye that are only partially visible to the surgeon, i.e., behind the iris where the lens haptic—depending on its shape—and the eye tissue have formed adhesions. Removal of such a lens can easily lead to severe eye injuries. Therefore, the peripheral lens haptic is frequently left in the eye.

Previously, there has been no ophthalmological instrument which, by means of an appropriate capturing device, would be capable of gripping the portion of the lens mount located behind the iris (mostly invisible), and cut it off the optical unit, in one single operation. To date, it was only possible to cut or nip off such lens loops. With the help of a second instrument (usually a forceps), it was then attempted to grip the separated portion and pull it from the eye.

SUMMARY OF THE INVENTION

This invention is based on the objective to develop an instrument of the above-mentioned kind in a way that would allow the gripping and clipping of the lens mount and its removal from the eye, all in one single operation.

In order to solve the problem, this invention is characterized by the fact that, at its tip, the tubular guide is equipped with a lateral opening which, at its face end, is closed off by a stop plate; that, parallel with the cutter, a holder is supported inside the tubular guide with axial motion that, independent of the cutter, can be moved to contact the stop plate.

Consequently, the essential feature of this invention is the fact that a basically known cutter that severs the artificial lens mount, based on this invention is coupled with a holding device. This is to say that an instrument is created for the removal of the lens mount (lens haptic) of artificial lenses that, in a single operation, severs the lens haptic inside the eye and grabs it with the second part of the instrument. As a result, this instrument permits the removal of the lens portion without the need to reenter the eye with a grabbing device (e.g., a forceps) and be faced with the problem of a hard-to-grab severed lens portion.

This invention therefore consists of the development of an instrument for removal of a lens where the instrument with its hook-shaped end accepts the lens loop. Initially, a pin is extended from a tubular guide located in front of it, to push the "captive" lens loop against the hook. Further compression of the holding device (i.e., a spring-loaded device), causes the cutting device to emerge from the instrument's tube. This cutting device is then shifted in parallel on one or the other side of the holding pin until it severs the lens haptic with its sharply ground end, while applying pressure to the above-mentioned hook-shaped end of the lens haptic, without losing the clipped part. The latter continues to be held in place by the holding pin thus allowing the instrument and the clipped-off lens portion to be removed from the eye.

A preferred version of this invention has the face end of the holder configured as a concave-shaped holding surface which substantially facilitates the clamping and holding of the lens mount.

Additional features of this invention are the subject of other secondary claims.

The innovative object of this invention results not only from the object of each individual patent claim, but also from the combination of all individual patent claims interactively. All data and features disclosed in the document—including the summary—particularly any geometric configurations presented in the drawings, are vital to the claims of this invention, provided they are a state-of-the-art novelty, whether individually or combined.

In the following this invention will be described in more detail using drawings that merely represent a typical application. Incidentally, these drawings and their descriptions reveal additional features and benefits vital to this invention.

BRIEF DESCRIPTION OF THE INVENTION

FIG. 1: Side view of an instrument according to this invention,

FIG. 2: Plan view of the instrument according to FIG. 1,

FIG. 3: Front view of the instrument according to FIGS. 1 and 2,

FIG. 4: Close-up 3-D view of the instrument tip,

FIG. 5: Schematic sectional view of the instrument's holder and cutter,

FIG. 6: Cross section VI—VI of FIG. 2.

DESCRIPTION OF THE PREFERRED EMBODIMENTS

Figure 4:
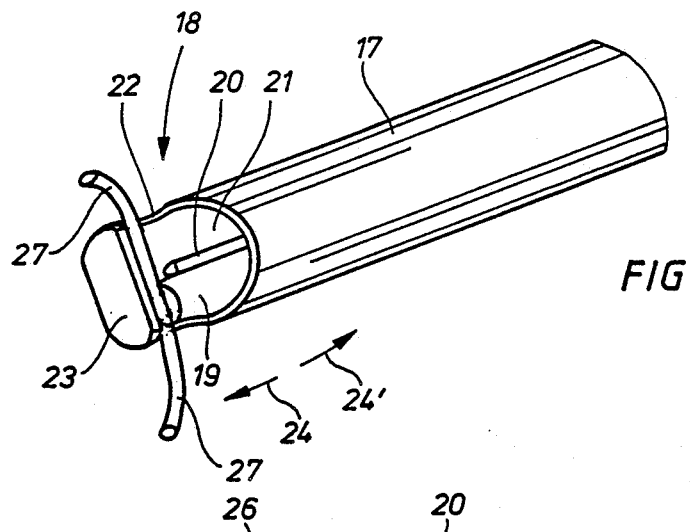

The invented instrument consists of a head with a tip 18 and a tubular guide 17, both extending from the front end of a guide housing 2. An actuator 3 is located behind the guide housing 2, which essentially is comprised of the handles 5, 6 and the carrier 4 associated with the handles.

The handles 5, 6 themselves are constructed similar to the handles of a forceps having serrations 13 on each of their surfaces.

At the rear end, the handles are assembled to a carrier 4 which is configured as a spring clip, using the spring force to effect the spreading of the handles 5, 6.

Extending from and following the centerline of the carrier 4, a guide bar 10 serves as a guide and support of the guide housing 2.

One pivot 9 is provided near the swing-out front end of each handle 5, 6, to which the one end of each lever 7, 8 is attached with unilateral rotation.

The other end of each lever is rotationally jointed to one of the clamping jaws 11, 12 (refer to FIGS. 1 and 3).

The clamping jaws 11, 12 are supported in the rear end of the housing 14, with sliding motion on the guide bar 10.

In the front end of the housing 14, the clamping jaws (refer to FIG. 6) are frictionally engaged with the holder 19 and the cutter 20.

A screw 15 is radially installed in the housing 14 and serves as a stop for the sliding drive.

At its front end, the housing 14 is reduced in diameter and continues as a sleeve 16 to which, with a further decrease in diameter, the tubular guide 17 is attached.

As can be seen from FIG. 2, the tubular guide 17 is slightly curved to permit its entry into the eye, as appropriate for the particular surgical procedure.

The tubular guide 17 provides axially sliding support for both the holder 19 and the cutter 20.

Figure 5:
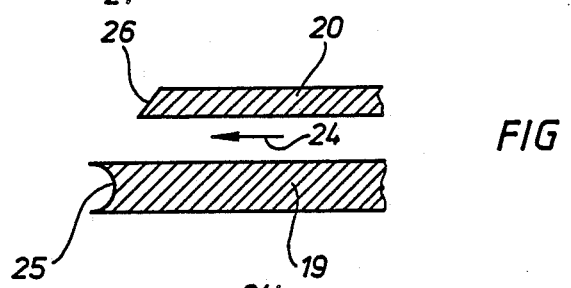

The holder 19 consists of a round tube which at its front face end features a concave holding surface 25, as seen in FIG. 5.

Adjacent to the holder 19, a cutter 20 is supported inside the tube 17, also with axially sliding motion, with the latter having a cutting edge 26 at its front face end.

The sliding drive for the two components will be described later.

Aside from using solid round profiles for the two components' construction, it is of course possible to use other profiles as, e.g., a tubular hollow profile, a triangular-profile tube, etc.

It must be emphasized that the tubular guide 17 is equipped with a lateral opening 22 at its tip 18 which is closed off by a stop plate 23 at its front face end. This stop plate then, is mounted perpendicular to the sliding motion (direction of arrow 24) of the holder 19 and the cutter 20. It is essential that, during sliding motion, both components 19, 20 will contact the inside of the stop plate 23.

Thus, the partially shown loop end 27 of a lens mount is entered sideways into the opening 22 until it comes to rest behind the stop plate 23, as outlined in FIG. 4.

It is assumed that at this time, holder 19 and cutter 20 are still retracted in direction of arrow 24'; they reside on the inside 21 of the tubular guide 17.

As soon as the loop end 27 is inserted in proper position into the opening 22, as seen in FIG. 4, the holder 19 is advanced in direction of arrow 24 to allow the concave holding surface 25 to surround and grip the loop end 27 at least partially. Subsequently, the cutter 20 is moved forward, also in direction of arrow 24, and severs the loop end while the remaining cut-off section is held tightly by the holder 19. The instrument is then withdrawn from the eye without any risk whatsoever of the loop end 27 separating from the tip 18, since the holder 19 with its holding surface 25 is in constant engagement with the cut-off loop end 27.

The handles 5, 6 are only actuated and the holder 19 is only retracted in the direction of arrow 24', into the tubular guide 17, after the instrument has been removed from the eye.

There are various solutions to the axial sliding drive for the holder 19 and the cutter 20.

It is particularly important to engage these two components with the loop end 27 to be treated, in succession.

This is to say that the holder 19 must first engage and clamp down on the loop end 27, which is followed by advancing the cutter 20 in direction of the arrow 24 in a manner allowing it to sever the loop end 27 with its cutting edge 26. The configuration of the actuator 3 in the style of a forceps is only mentioned here as an example. Alternatively, instead of having the two handles 5, 6 moving toward each other, some appropriate guide sleeves may be used, with the holder 19 extending in the form of a sleeve, immediately from the rear end of the instrument, similar to the cutter 20, while both rods may be actuated directly by hand, independent of each other.

The following however, is a detailed description of the actuator 3 shown in the drawings.

Based on the fact that the levers 7, 8 are jointed to the pivot 9 on the freely moving end of each handle 5, 6 and, on their other end, directly attached to the clamping jaws 11, 12 by means of a pivot not described in detail, an axial sliding drive is created for the clamping jaws 11, 12. It is significant though, that the levers 7, 8 be installed at a slightly forward-pointing angle, in direction of the arrow 24, in order to support a sliding motion of the clamping jaws 11, 12 in direction of arrow 24 (forward) when the handles 5, 6 are compressed.

Figure 6:
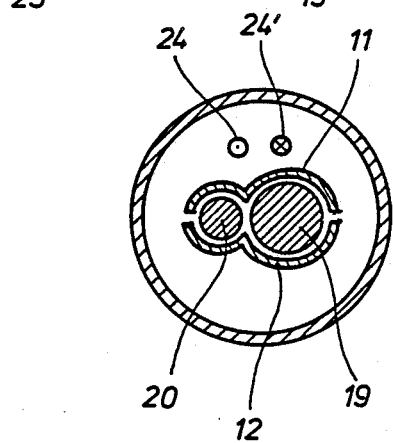

As shown in FIG. 6, one clamping jaw 11, 12 each is frictionally engaged with the surface of the holder 19 and the cutter 20. The frictional engagement may be further enhanced by means of a circumferential spring, rubber band, etc.

It goes without saying that, instead of the side-by-side arrangement, the two components may also be installed coaxially nested inside the tubular guide 17.

I claim:

1. An instrument for removal of at least a portion of an intraocular lens from an eye, the intraocular lens having a lens body and at least one haptic member, said instrument comprising:
    a housing member;
    an elongated hollow probe portion connected to the housing member, said probe portion having an opening adjacent its outer end and a stop means;
    holder means positioned in said hollow probe portion and being movable to contact said stop means and to securely hold a haptic member positioned in said opening against said stop means; and
    cutter means positioned in said hollow probe portion and being movable toward said stop means, said cutter means being used to sever a haptic member positioned in said opening against said stop means.

2. The instrument as set forth in claim 1 further comprising means connected to said housing member to move said holder means and said cutter means axially in said hollow probe portion towards and away from said stop means.

3. The instrument as set forth in claim 2 wherein said means to move said holder means and said cutter means comprises manually activatable handle and lever means.

4. The instrument as set forth in claim 1 wherein said holder means and said cutter means are positioned adjacent one another in said probe portion.

5. The instrument as set forth in claim 1 wherein said holder means has a concave-shaped holding end.

6. The instrument as set forth in claim 1 wherein said holder means and said cutter means operate independently of one another.

7. The instrument as set forth in claim 1 further comprising sliding drive means for activation and operation of said holder means and said cutter means.

8. The instrument as set forth in claim 7 wherein said sliding drive means comprises two opposing clamping members which frictionally engage the holder means and said cutter means.

9. The instrument as set forth in claim 8 further comprising handle and lever means for operating said sliding drive means.

10. The instrument as set forth in claim 9 wherein said housing member is rotatable and said handle and lever means are connected at one end to said housing member and connected to said sliding drive means clamping members at the other end.

11. The instrument as set forth in claim 1 wherein said probe member is flexible.

12. An instrument for removal of at least a portion of an intraocular lens from an eye, the intraocular lens having a lens body portion and at least one haptic member thereon, said instrument comprising:
   a handle means;
   a hollow probe member connected at one end to said handle means and having an opening at the other end;
   a stop member positioned in said opening in said probe member;
   a cutter member slidably positioned in said probe member;
   a holder member slidably positioned in said probe member;
   clamping means in said handle means for gripping said cutter member and said holder member; and
   actuator means on said handle means and connected to said clamping means for operating said clamping means to selectively grip and axially move said cutter member and said holder member in said probe member;
   whereby a haptic member positioned in said opening in said probe member is first held against the stop member by said holder member as activated by said actuator means, and then said haptic member is severed by said cutter member as subsequently activated by said actuator means.

13. The instrument as set forth in claim 12 wherein said probe member is flexible.

14. An instrument for grasping, cutting and removing an intraocular lens haptic member from an eye, the instrument comprising:
   a housing member;
   a tubular probe member connected at one end to the housing member at one end and having a lateral opening at the other end;
   stop means positioned in said opening;
   haptic holding means slidably positioned in said probe member;
   haptic cutting means slidably positioned in said probe member adjacent said haptic holding means; and
   means for gripping and moving said holding means and said cutting means;
   whereby said holding means grasps the haptic member and said cutting means severs the haptic member.

15. The instrument as set forth in claim 14 wherein said stop means comprises the outer end of said probe member.

16. The instrument as set forth in claim 14 wherein said means for gripping and moving said holding means and said cutting means comprises manually actuatable handle and lever means and sliding drive means.

17. A method of removing at least a portion of an intraocular lens from an eye using an instrument having a handle portion, a probe portion, a cutter means and a holder means, said intraocular lens having a body portion and at least one haptic member, said method comprising the steps of:
   inserting said probe into the eye;
   capturing said haptic member with said holder means;
   cutting said haptic member with said cutter means; and
   removing said probe portion from the eye together with the captured haptic member in the instrument.

18. A method of removing an intraocular lens from an eye with an instrument, said intraocular lens having a body portion and at least one haptic member, and said instrument having a probe portion with an opening therein and a stop means, a cutter member and a holder member, said method comprising the steps of:
   inserting said probe portion of said instrument into said eye;
   positioning said instrument such that the haptic member of the intraocular lens is positioned in said opening;
   moving said holder member to hold said haptic member in said probe portion against said stop means;
   moving said cutter member to sever said haptic member adjacent said holder member; and
   removing said probe portion from the eye together with at least the portion of the haptic member held in said probe portion by said holder member.

19. The method of claim 18 wherein said body portion of the intraocular lens is connected to said portion of the haptic member held in said probe portion and is removed from said eye by said instrument together with said portion of the haptic member.

* * * * *